United States Patent
Leuschner et al.

(10) Patent No.: US 11,031,127 B2
(45) Date of Patent: Jun. 8, 2021

(54) MONITORING THE EXPOSURE OF A PATIENT TO AN ENVIRONMENTAL FACTOR

(71) Applicant: KONINKLIJKE PHILIPS N.V., Eindhoven (NL)

(72) Inventors: Katja Leuschner, Amsterdam (NL); Mun Hum Park, Eindhoven (NL); Andre Melon Barroso, Aachen (DE); Frank Mueller, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 611 days.

(21) Appl. No.: 15/535,441

(22) PCT Filed: Dec. 15, 2015

(86) PCT No.: PCT/EP2015/079816
§ 371 (c)(1),
(2) Date: Jun. 13, 2017

(87) PCT Pub. No.: WO2016/096872
PCT Pub. Date: Jun. 23, 2016

(65) Prior Publication Data
US 2017/0364648 A1    Dec. 21, 2017

(30) Foreign Application Priority Data
Dec. 16, 2014  (EP) .................................... 14198307

(51) Int. Cl.
*G16H 40/63*   (2018.01)
*G16H 10/60*   (2018.01)
(Continued)

(52) U.S. Cl.
CPC ............ *G16H 40/63* (2018.01); *A61B 5/4806* (2013.01); *G16H 10/60* (2018.01); *G16H 20/00* (2018.01); *G16H 20/70* (2018.01)

(58) Field of Classification Search
None
See application file for complete search history.

(56) References Cited

U.S. PATENT DOCUMENTS

| 9,659,149 B2 | 5/2017 | Kohlrausch et al. |
| 2005/0085738 A1* | 4/2005 | Stahmann ............ A61B 5/4806 600/529 |

(Continued)

FOREIGN PATENT DOCUMENTS

| RU | 2150301 C1 | 6/2000 |
| WO | 2012176098 A | 12/2012 |

(Continued)

OTHER PUBLICATIONS

B. Berglund et al., Guidelines for Community Noise, 1999, World Health Organization (Year: 1999).*

(Continued)

*Primary Examiner* — Aryan E Weisenfeld
*Assistant Examiner* — Karen A Hranek

(57) ABSTRACT

The invention suggests a system for monitoring the exposure of a patient (1) to at least one environmental factor. The system particularly comprises a database (8) storing an environmental prescription for the patient, the environmental prescription specifying a maximum level of the environmental factor and a minimum duration for the level of the environmental factor to be smaller than the maximum level, and an evaluation module (7) configured to detect on the basis of a measurement signal and the stored environmental prescription a time interval in which a level of the environmental factor is below the maximum level and to compare the duration of the detected time interval with the minimum (Continued)

duration. On the basis of the result of this comparison, healthcare staff can plan activities in such a way that the patient is provided with a rest period substantially having the minimum duration.

18 Claims, 2 Drawing Sheets

(51) Int. Cl.
*G16H 20/00* (2018.01)
*G16H 20/70* (2018.01)
*A61B 5/00* (2006.01)

(56) References Cited

U.S. PATENT DOCUMENTS

| | | | |
|---|---|---|---|
| 2006/0012478 A1* | 1/2006 | Carmichel | G08B 3/10 340/552 |
| 2008/0015463 A1* | 1/2008 | Goldstein | H04R 29/008 600/559 |
| 2009/0052677 A1* | 2/2009 | Smith | H04R 29/008 381/56 |
| 2014/0254808 A1 | 9/2014 | Park et al. | |
| 2015/0031942 A1 | 1/2015 | Lashina et al. | |

FOREIGN PATENT DOCUMENTS

| | | | | |
|---|---|---|---|---|
| WO | WO-2013057608 A1 * | 4/2013 | | A61B 5/0077 |
| WO | WO-2013057652 A2 * | 4/2013 | | |

OTHER PUBLICATIONS

M. Park et al., Noise in hospital rooms and sleep disturbance in hospitalized medical patients, Aug. 18, 2014, Environmental Health and Toxicology, vol. 29 (Year: 2014).*

Park, M. et al., "Noise in hospital rooms and sleep disturbance in hospitalized medical patients", Environmental Health and Toxicology, vol. 29, Aug. 18, 2014, p. e2014006.

Kowalczyk, L, "Hospital noise hinders recovery", The Boston Globe, Oct. 31, 2011, pp. 1-5.

Joseph, A. et al., "The impact of Light on Outcomes in Healthcare Settings for Health Design issue Paper #2", Issue Paper #2, Aug. 1, 2006, pp. 1-12.

Mercola, Dr., "Hospital Room Lighting May Worsen Your Mood and Pain", Mercola.com—Take Control of Your health, Dec. 26, 2013, pp. 1-4.

* cited by examiner

MONITORING THE EXPOSURE OF A PATIENT TO AN ENVIRONMENTAL FACTOR

CROSS-REFERENCE TO PRIOR APPLICATIONS

This application is the U.S. National Phase application under 35 U.S.C. § 371 of International Application No. PCT/EP2015/079816, filed on Dec. 15, 2015, which claims the benefit of European Patent Application No. 14198307.2, filed on Dec. 16, 2014. These applications are hereby incorporated by reference herein.

FIELD OF THE INVENTION

The invention relates to a system and a method for monitoring an exposure of a patient to at least one environmental factor, such as noise or light. Moreover, the invention is related to a computer program causing a processing unit to carry out the method.

BACKGROUND OF THE INVENTION

The comfort and the recovery of ill patients are greatly influenced by the exposure of patients to noise, light and other environmental factors. For instance, studies have shown that hospitals are noisy places and lowering the noise levels can lead to a shorter length of stay in a hospital. In this respect, the patients' comfort can be increased and their recovery can be improved, when the patients are exposed less frequent to environmental factors such as noise and light, which exceed disturbing levels.

However, in hospitals and other healthcare facilities, it is difficult to control the environmental factors, because these are often intrinsically linked with the operations necessary to provide services to the patients. As a consequence, patients are relatively frequently exposed to disturbances by noise, light and similar environmental factors, which can be avoided only to a limited extent. For example, noise produced by ventilators or monitor alarms cannot be avoided, staff cannot care for a patient in a dark patient room, and staff needs to communicate during work which leads to noise due to voice. Disturbances are caused at least to some extent by activities of healthcare staff, the staff visiting each patient several times a day in order to care for them regarding their basic needs and to provide medical treatments.

Often, these activities of the healthcare staff prevent the patients from having the required longer rest periods. In this respect, an improved planning of such activities could allow for providing the required rest periods to the patients.

SUMMARY OF THE INVENTION

It is an object of the invention to enable healthcare staff to act in a way such that their patients can have longer rest periods and ideally can have the rest periods which are needed for their recovery. It has been found by the inventors, that activities of healthcare staff which produce noise or require light are often not well coordinated with the patients' needs for rest and sleep. Accordingly it is a further objective of the invention to provide automated assistance to healthcare staff for planning activities in such a way that the patient has a certain longer rest period.

In a first aspect of the invention, a system for monitoring the exposure of a patient to at least one environmental factor is suggested. The system comprises a receiver module for receiving a measurement signal representing a level of the environmental factor in a vicinity of the patient. Further, the system comprises a database for storing an environmental prescription for the patient, the environmental prescription specifying a maximum level of the environmental factor and a minimum duration for the level of the environmental factor to be smaller than the maximum level. Moreover, the system comprises an evaluation module configured to compare the level of the environmental factor with the maximum level on the basis of the measurement signal, to detect on the basis of the comparison a time interval in which a level of the environmental factor is substantially permanently below the maximum level and to compare a duration of the detected time interval with the minimum duration.

The proposed environmental prescription corresponds to an instruction to provide a rest period of the minimum duration to the patient, where in this context the term rest period denotes a time interval in which a level derived from the measurement signal is below the maximum level specified in the environmental prescription. Since the evaluation module can detect such a rest period and compare the duration of the detected rest period with the minimum duration, the system can assist the healthcare staff to schedule activities, which potentially interrupt or terminate the rest period, in such a way that the patient has a longer rest period with at least the minimum duration specified in the environmental prescription.

For example, the healthcare staff may completely refrain from such activities (if they are not necessary e.g. to keep or restore the patient's health) during a detected ongoing rest period and may schedule such activities for a point in time when the minimum duration has expired for the ongoing rest period. In accordance with another possible strategy, the healthcare staff may refrain from activities disturbing the patient when the detected ongoing rest period already has a significant length and when there is a significant difference between the duration of the ongoing rest period and the minimum duration specified in the environmental prescription. This strategy is based on the assumptions that (i) the patient can recover in a new rest period when the ongoing rest period does not have a significant length and that (ii) it may be acceptable that the patient has a rest period with a slightly shorter duration than the minimum duration specified in the environmental prescription.

In both aforementioned examples, the healthcare staff can plan its activities on the basis of the evaluation of the measurement signal in the evaluation module, i.e. the detection of an ongoing rest period and the comparison of the duration of the detected rest period with the minimum duration in the environmental prescription.

Preferably, the evaluation module is further configured to control at least one output unit to output information representative of the result of the comparison between the detected period of time and the minimum duration. Thus, the healthcare staff can particularly plan activities that potentially disturb the patient on the basis of the information provided by the output unit.

The proposed system can be used for monitoring any suitable environmental factor affecting the patient. In particular, the system can be used to monitor environmental factors which are not completely but to some extend influenced by the healthcare staff. In specific embodiments, the environmental factor is noise or light.

Preferably, the evaluation module detects a time interval, in which the level of the environmental time is substantially permanently below the maximum level, when the level of the environmental factor does not exceed the maximum level in the time interval. In a further embodiment, the evaluation module is configured to detect a time interval in which the level of the environmental factor is substantially permanently below the maximum level if the level of the environmental factor is permanently below the maximum level during the time interval except for one or more sections of the time interval, which are shorter than a predetermined duration. In this embodiment, the evaluation module does also detect a rest period in case of transgressions of the maximum level of the environmental factor which do not last longer than a predetermined duration. This duration is preferably defined relatively short. Thus, in these embodiments, it can be taken account of the fact that short noise "peaks" do usually not strongly disturb the patient.

In a related embodiment, the predetermined duration is defined as function of the level of the environmental factor. Thus, it is e.g. possible to define shorter durations for higher levels of the environmental factor exceeding the maximum level specified in the environmental prescription.

In one embodiment, the environmental prescription specifies at least one period of time in which the level of the environmental factor should be smaller than the maximum level for the minimum duration and wherein the evaluation module is configured to check whether the level of the environmental factor is smaller than the maximum level for the minimum duration within the period of time. The period of time specified in the environmental prescription may particularly correspond to a predetermined day or to predetermined hours on a certain day. Thus, it is e.g. possible to specify that the patient should have a rest period of six hours at a certain day particularly without having to specify the start time for the rest period. Hence, the patient can have the rest period in accordance with his needs and with schedule of the care for the patient which does usually not allow a rest period to occur at any time.

In a further embodiment, the environmental prescription specifies a plurality of periods of time and specifies for each of the plurality of periods of time an associated maximum level of the environmental factor and an associated minimum duration for the level of the environmental factor to be smaller than the associated maximum level, and the evaluation module is configured to detect in each of the plurality of periods of time a time interval in which the level of the environmental factor is below the maximum level associated with the period of time and to compare the detected time interval with the minimum duration associated with the period of time. This embodiment does particularly allow for specifying individual minimum durations of the rest period for different periods of time in which the rest periods shall occur.

Moreover, one embodiment provides that the database stores at least one further environmental prescription for a further patient, the further environmental prescription comprising a different maximum level of the environment factor and/or a different minimum duration for the level of the environmental factor to be smaller than the maximum level. This embodiment makes it possible to specify for each of a plurality of patients an individual maximum level for the level of the environmental factor and/or an individual minimum duration for the level to be smaller than the maximum level. Hereby, it is particularly possible to adapt the maximum level or the minimum duration to the patient's condition.

In one embodiment, the environmental factor is noise and the environmental prescription specifies individual maximum noise levels for sound categories of sound events, wherein the evaluation module is configured to detect a sound event on the basis of the measurement signal and to determine a sound category for the detected sound event and wherein the evaluation module is configured to detect a time interval in which a level of the environmental factor is below the maximum level on the basis of a comparison between a noise level determined for the sound event and the maximum noise level specified for the sound category of the sound event. In this embodiment, the maximum noise level for sound events which are not under the control of the healthcare staff may particularly be set higher than the maximum noise level for sound events produced by the healthcare staff. Hereby, is made easier for the healthcare staff to fulfill the environmental prescription.

Furthermore, one embodiment provides that the system further comprises a measurement device for substantially continuously monitoring the environmental factor in the vicinity of the patient, the measurement device being adapted to provide the measurement signal. In particular, the measurement device monitors the environmental factor in such a way that it performs a continuous measurement or that it performs measurements in short time intervals.

In a related embodiment, the measurement device is comprised in a patient monitor, the patient monitor being further configured to monitor at least one vital sign of the patient. In this further embodiment, the measurement device of the system can easily be integrated into a patient monitor which usually already exists in intensive care units (ICUs), for example.

In a further aspect of the invention, a method for monitoring the exposure of a patient to least one environmental factor is proposed. The method comprises the steps of:
receiving a measurement signal representing a level of the environmental factor in a vicinity of the patient,
obtaining an environmental prescription for the patient, the environmental prescription specifying a maximum level of the environmental factor and a minimum duration for the level of the environmental factor to be smaller than the maximum level,
comparing the level of the environmental factor with the maximum level on the basis of the measurement signal,
detecting on the basis of the comparison a time interval in which the level of the environmental factor is substantially permanently below the maximum level, and
comparing the detected time interval with the minimum duration.

In a still further aspect of the present invention, a computer program is presented. The computer program is executable in a processing unit of a system as defined in claim 1, and the computer program comprises program code means for causing the processing unit to carry out a method as defined in claim 13.

It shall be understood that the system of claim 1, the method of claim 13 and the computer program of claim 14 have similar and/or identical embodiments, in particular as defined in the dependent claims.

It shall be understood that an embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
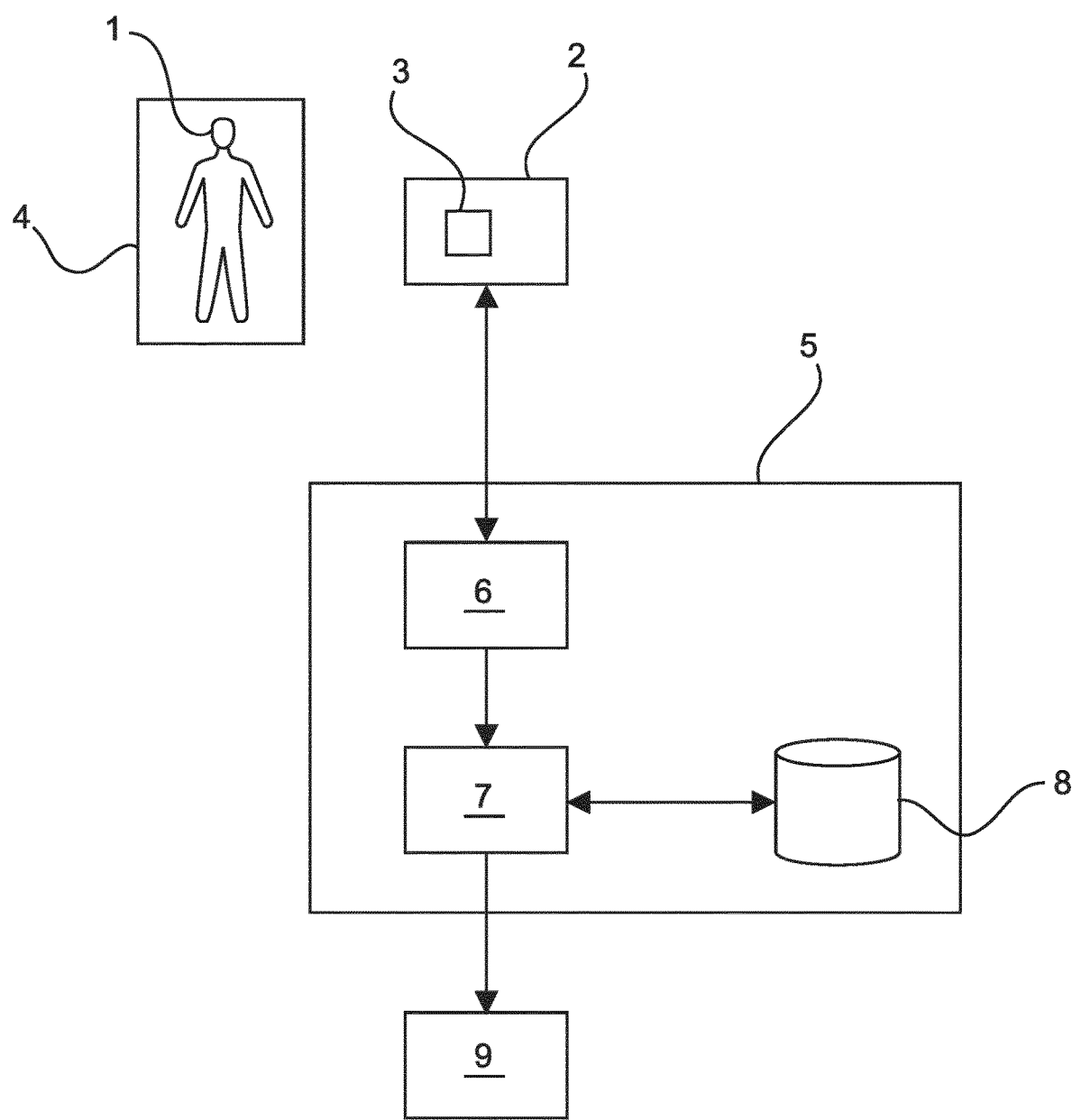
FIG. 1 shows schematically and exemplarily an embodiment of a monitoring system for monitoring the exposure of a patient to an environmental factor.

FIG. 1 shows schematically and exemplarily components of a system for monitoring the exposure of a patient 1 to an environmental factor. The monitoring system may be operated in a department of a hospital, particularly in an ICU of a hospital. Likewise, the system may be operated in another healthcare facility, where a patient is frequently visited by healthcare staff. As will be described in more detail herein below, the system provides automated help assistance for healthcare staff to plan visits of the patient and other activities in such way that the patient 1 has sufficient recovery periods without disturbances in accordance with an environmental prescription for the patient 1.

In the following, the monitoring system will be described with respect to the monitoring and evaluation of noised affecting the patient 1. However, the system may be used in a similar way to monitor and evaluate the exposure of the patient 1 to one or more other environmental factors, such as light. Moreover, the system will particularly be described with respect to the monitoring and evaluation of one patient's exposure to noise. It will be understood, though, that the system can simultaneously monitor and evaluate the exposure of further patients 1 to noise in an analogue way.

In order to determine the patient's exposure to noise, the system comprises a measurement device 2 for measuring a quantity representing the noise level in the vicinity of the patient 1. For this purpose, the measurement device 2 may comprise a noise sensor 3 which may be positioned in the area of the bed 4 of the patient 1. In particular, the noise sensor 3 may be a microphone measuring sound a manner known to the person skilled in the art. The noise sensor 3 is configured to substantially continuously measure the quantity to thereby produce a noise measurement signal which particularly shows the variation of noise in the patient's vicinity with time. This means that the noise sensor 3 captures the noise level continuously or in small time intervals. The measurement signal provided by the measurement device 2 may include the measured values of the quantity monitored by the measurements device 2, or it may include changes of these values.

In an ICU, there is usually a bedside monitor for each patient 1 which particularly monitors the patient's vital signs. In one embodiment of the monitoring system, the measurement device 2 may be integrated into the patient's bedside monitor. However, it is likewise possible to configure the measurement device 2 as a separate device positioned in the vicinity of the patient's bed 4.

In one embodiment, the noise sensor 3 is configured as a microphone. On the basis of the measurements signal the noise level in the vicinity of the patient can be derived. Moreover, it is possible to determine the kind and/or source of the noise as will be explained in more detail below.

Further, the system comprises a monitoring device 5 for evaluating the measurement signal provided the measurement device 2. The monitoring device 5 may be configured as a data processing apparatus in which functions for evaluating the measurement signal and related functions are implemented in the form of software modules.

In one embodiment, the monitoring device 5 is configured as a central device which is located remote from the measurement device 2 and which is connected to the measurement device 2 via a data network or another suitable data connection. In this embodiment, the monitoring device 5 may be connected to a plurality of measurement devices 2 monitoring the noise levels in the vicinity of a plurality of patients 1. In this case, the monitoring device 5 may evaluate the measurement signal of each measurement device 2 on the basis of an environmental prescription for the patient 1 associated to the respective measurement device 2. In an alternative embodiment, the monitoring device 5 may only evaluate the measurement signal provided by one measurement device 2. Other measurement signals may be evaluated in further monitoring devices 5 which may be configured analogously. In this case, the measurement device 2 and the monitoring device 5 may be part of an integrated apparatus. In particular, both devices may be integrated into the patient's bedside monitor, when such bedside monitor is provided.

The monitoring device 5 comprises a receiver module 6 for receiving the measurement signal provided by the measurement device 2. The evaluation of the measurement signal on the basis of the environmental prescription for the patient 1 is made in an evaluation module 7 of the monitoring device 5.

The evaluation module 7 obtains the environmental prescription for the patient 1 from a prescription database 8 which may be integrated into the monitoring device as illustrated in FIG. 1 or which may be connected to the monitoring device 5 via a data network or another suitable data connection. The prescription database 8 may store environmental prescriptions for a plurality of patients 1. This may particularly be the case if the monitoring device 5 is configured as a central device evaluating the measurement signals for a plurality of patients 1.

In accordance with the results of the evaluation of the measurement signal, the evaluation module 7 controls at least one output unit 9. Preferably, the output unit 9 is configured as a display device providing visual information corresponding to the result of the evaluation. In addition, the output unit 9 may be configured to provide an acoustic output in accordance with the result of the evaluation made in the evaluation module 7. The output unit 9 may be located remote from the patient's bed 4, preferably outside the patient's room. Such an arrangement of the output unit 9 allows the healthcare staff to view the provided information about rest periods for the patient 1 without having to make a potentially disturbing visit of the patient 1. In particular, the output unit 9 may be located in the nursing station of the healthcare facility's department taking care of the patient 1 and/or in a corridor in front of the patient's room.

In a further embodiment, the evaluation module 9 controls a plurality of output units 9 to show information corresponding to the evaluation of the measurement signal in the evaluation module 7. In this embodiment, one output unit 9 may be located in the patient's room in addition to one or more further output unit(s) located in the nursery station and/or another location, such as the corridor in front of the patient's room. Here, the output unit 9 in the patient's room may be integrated into the bedside monitor of the patient 1.

It shall be understood that the single output unit 9 or the plurality of output units 9 are not necessarily used for exclusively showing information provided by the evaluation module 7 of the monitoring device 5. Rather, the output unit(s) 9 may additionally show further information, particularly information relating to the patient 1. In case the patient 1 is cared in an ICU, where also the patient's vital signs are monitored, the output units 9 may show the information provided by the evaluation module 7 in addition to the vital signs, for example.

The environmental prescription for the patient 1 does at least specify a maximum noise level which is also referred to as noise threshold herein below and a minimum duration for which the noise level shall be below the maximum level. This information particularly corresponds to a prescription of a rest period having at least the minimum duration. Preferably, the environmental prescription does also specify one or more period(s) of time during which the patient 1 shall have a rest period. These periods of time may be days corresponding to a certain dates or the periods of time may correspond to hours at certain dates. These hours may particularly correspond to daytime and nighttime so that for daytime and nighttime different rest periods can be specified. Thus, the environmental prescription may correspond to a kind schedule for prescribed rest periods for the patient 1.

In a specific example comprising equal rest periods for several days, the environmental prescription for a patient 1 may provide one rest period of five hours each day or it may provide one rest period of two hours between eight o'clock in the morning and six o'clock in the evening (i.e. during daytime) and a further rest period of four hours between eight o'clock in the evening and six o'clock in the morning (i.e. during nighttime) each day. In a further example comprising different rest periods for several days, the environmental prescription for the patient 1 may provide a rest period of ten hours at the first day of his stay in the hospital, a rest period of eight hours at his second day of stay and a rest period of six hours on his third and fourth day of stay. By defining different rest periods for several days, account can be taken of the fact that patients 1 often require shorter rest periods when their health status improves.

The duration and timing of the rest periods are preferably specified individually for each patient 1 in the environmental prescription assigned to the patient. The specification may be made by a physician and/or by a medical algorithm on the basis of medical knowledge and on the basis of the patient's conditions including the patient's age, the patient's physical condition and the severity of the patient's illness or injury.

The maximum noise level included in the environmental prescription for a patient 1 may likewise be specified individually for each patient. In particular, the maximum noise level for a patient 1 may be set to a maximum value which does not disturb the patient in accordance with the patient's ability to perceive sounds. So, a higher maximum noise level may be specified for a hearing-impaired patient 1 as compared to a normal-hearing patient 1. By such a differentiation with respect to the noise threshold, it can be ensured that each individual patient 1 is not disturbed during the rest period. At the same time, the healthcare staff is not prevented from actions which cause noise but do not affect a patient 1 due to the patient's decreased hearing ability. So, it may not be possible to visit the patient's room without causing noise above the maximum noise level for a normal-hearing patient 1, but it may be possible to visit the room of a hearing-impaired patient 1 without violating the higher noise threshold set for this patient 1.

Moreover, it is possible to specify different maximum noise levels for different rest periods included in the environmental prescription. In this respect, a higher maximum noise level may e.g. be specified for the one or more rest period(s) for a patient on the first day after a surgery or part of the first day after a surgery. The reason may be that the patient is still under the influence of an anesthetic in this period of time and, thus, less sensitive to noise.

In a further embodiment, the monitoring system is capable of detecting and categorizing sound events in the measurement signal provided by the measurement device 2. Possible sound categories include alarms of medical devices such as bedside monitors, speech, staff activity and one category for other sounds. In the environmental prescription may specify an individual noise threshold for each sound category or for certain groups of sound categories. In this regard, a higher noise threshold may be specified for categories corresponding to unavoidable noise, such as, for example alarms. A lower noise threshold may be specified for categories corresponding to avoidable noise, such as, for example, speech. Such a specification of different noise thresholds makes it easier for the healthcare staff to fulfill the environmental prescription for the patient 1. In particular, it possible for the healthcare staff to fulfill a environmental prescription including such a specification of different noise thresholds by only avoiding noise which is actually produced under the influence of the healthcare staff.

The determination of the sound category for a certain sound event detected in the measurement signal of a measurement device 2 may be made in the evaluation module 7 on the basis of an evaluation of the frequency spectrum of the measurement signal. In addition, the evaluation module 7 may be capable of determining correlations between the sound signals captured by plural measurement devices 2 connected to the monitoring device 5. If the evaluation module 7 finds a strong correlation of such sound signals, it may determine that the corresponding sounds originate from the same source. On the basis of the sound levels of such correlated sound events, the evaluation module 7 may then approximate the location of the sound source. This information about the approximate location of the sound source may be used to determine the sound category in addition to the information derived from the frequency spectrum.

Exemplary procedures for determining the sound category, which may be used by the evaluation module 7, are also described in the international patent applications WO 2013/057652 and WO 2013/057608.

The environmental prescription for a patient 1 configured in the aforementioned way may be understood as a recommendation for the healthcare staff, which the heath care staff should try to fulfill with the assistance of the monitoring system. Thus, the healthcare staff should try to plan its activities in such way that the patient has the rest periods specified in the patient's environmental prescription. Hereby, the convalescence of the patient can be accelerated and improved in further respects. However, it will typically not be required that the environmental prescription is strictly observed by the healthcare staff. In particular, it is to be understood that the environmental prescription shall not prevent the healthcare staff from necessary actions for keeping and/or responding the patient's health, such as visits to the patients in case of potential emergencies.

For evaluating the measurement signal captured by the measurement device 2 located in the vicinity of a certain patient 1, the evaluation module 7 obtains the environmental prescription for the patient 1 from the prescription database 8. Moreover, the evaluation module 7 determines from the environmental prescription the specification for a rest period which is relevant for the time of the evaluation. Thus, the evaluation module 7 determines from the environmental prescription the periods of time for which associated rest periods are specified. From these periods of time, the evaluation module 7 selects the period of time which corresponds to the time of the evaluation.

At least as long as the prescribed rest period for the relevant period of time (i.e. the period of time in which the evaluation is made) has not been completed the evaluation module 7 evaluates the measurement signal provided by the measurement device 2 substantially continuously. In particular, this means that the evaluation module 7 evaluates the measurement signal in consecutive evaluation steps, which have a small enough time difference. In each evaluation step, the evaluation module 7 compares a noise level derived from the measurement signal with the noise threshold specified in the environmental prescription for the rest period in the relevant period of time.

In one embodiment, the noise level derived from the measurement signal corresponds to the signal level at the time the evaluation step is carried out. However, it is likewise possible to derive the noise level from the measurement signal in another way. For example, the evaluation module 7 may calculate average noise levels for consecutive intervals of the measurement signal. The intervals may have a length of one or several minutes, for example. In principle, it is possible to derive the noise level from the measurement signal in any way known to a person skilled in the art.

If the evaluation module 7 is capable of detecting and categorizing sound events in the measurement signal, the noise level derived by the evaluation module 7 from the measurement signal corresponds to the level of the dominant (i.e. loudest) detected sound event in the measurement signal. This noise level is then compared to the noise threshold specified in the environmental prescription for sound events having the category determined in the evaluation module 7 for the detected sound event.

In case the comparison between the noise level derived from the measurement signal and the relevant noise threshold specified in the environmental prescription results in the determination that the noise level is above the maximum noise threshold, the evaluation module 7 judges that no rest period is in progress. In response to such a judgment, the evaluation module 7 may optionally control the output unit 9 to show a corresponding indication. This indication may also inform the healthcare staff that a rest period of the duration specified in the environmental prescription is prescribed for the patient 1 and that this rest period should occur within the period of time specified in the environmental prescription. Also, the evaluation module 7 may calculate the difference between the remaining duration of the period of time and the prescribed duration of the rest period and control the output unit 9 to output this difference. Thus, the healthcare staff is informed about the reaming time until the rest period for the patient should begin. In addition, an information indicative of the noise level derived from the measurement signal may be output.

When the evaluation module 7 determines in one evaluation step that the noise level derived from the measurement signal is below the relevant maximum noise level specified in the environmental prescription, the evaluation module 7 judges that a rest period is in progress. In this case, the evaluation module 7 further determines the duration of the ongoing rest period.

For determining this duration, the evaluation module 7 may start a timer in the evaluation step in which it has derived a noise level below the prescribed maximum noise level for the first time. In each following evaluation step in which the evaluation module 7 derives a noise level from the measurement signal, which is below the prescribed threshold, the timer is incremented. Thus, the value of the timer in each evaluation step corresponds to the past duration of the ongoing rest period. This value is read from the timer by the evaluation module 7 in order to determine the past duration of the ongoing rest period.

Alternatively, the past duration of the ongoing rest period is determined in another way. For example, the evaluation module 7 may store the time when it determines for the first time that the noise level derived from the measurement signal is below the relevant prescribed noise threshold. In each subsequent evaluation step, in which the evaluation module 7 determines that the derived noise signal is still below the prescribed noise threshold, it may then compare the current time with the stored time. On the basis of the difference between both times, the evaluation module 7 may determine the past duration of the ongoing rest period.

In one embodiment, the rest period can also include one or more small time intervals of a predetermined maximum duration, in which the noise level exceeds the maximum level. If several such time intervals occur, a rest period may be detected when these time intervals are at least separated by a predetermined time distance. The maximum duration may be between several seconds and one minute, for example. The predetermined time distance between the time intervals may be between ten minutes and one hour or several hours, for example. Optionally, the maximum duration may also be defined as a function of the difference between the maximum level and the noise level, which may be stored in the evaluation module 7. In this configuration, the rest period may include a tunic interval of a first predetermined duration in which the noise level exceeds the maximum level by a first maximum amount and/or a time interval of a second predetermined duration in which the noise level exceeds the maximum level by a second maximum amount. Moreover, an ultimate noise threshold may be defined which may not be exceeded. Thus, when the evaluation module 7 determines a noise level above the ultimate noise threshold during an ongoing rest period, it may detect an end of the period irrespective of the time interval in which the noise level exceeds the ultimate noise threshold.

In these embodiments, the evaluation module 7 does also continue to detect an ongoing rest period and to determine its past duration in an analogue manner as described above, when the noise level exceeds the maximum level for one or more short time durations. Hereby, it is taken account of the fact that short noise "peaks" do often not strongly disturb the patient, and the healthcare staff is given the opportunity to perform necessary action involving an increased noise level for a short period of time without interrupting the detection of an ongoing rest period. Also, it is e.g. possible for the healthcare staff to close the door of the patient's room (what may involve a certain noise "peak") in order to protect the patient 1 from expected noise outside the patient's room.

Upon having determined the past duration of the ongoing rest period, the evaluation module 7 compares the determined past duration with the duration of the rest prescribed for the patient in the environmental prescription. On the basis of this comparison, the evaluation module 7 determines the difference between both durations, which corresponds to the time that is still required in order to complete the ongoing rest period such that the environmental prescription is fulfilled.

When the evaluation module 7 has determined in one evaluation step that a rest period is in progress and upon having determined the past duration of the ongoing rest period and the difference between this duration and the duration of the prescribed rest period in the relevant period of time, this information is output by the output unit 9 under the control of the evaluation module 7. The difference between the past duration of the ongoing rest period and the duration of the prescribed rest period may particularly be output in the form of an absolute time value and/or in the form of an indication, such as a percentage value, which represents the portion of the prescribed rest period which is elapsed within the ongoing rest period. For example, if a rest period of three hours is specified in the environmental prescription and if the evaluation module 7 determines a past duration of one hour for the ongoing rest period, an information may be output by the output unit 9 that the rest period would have to be maintained for two further hours for fulfilling the environmental prescription and/or that the past duration of the ongoing rest period corresponds to 33% of the duration of the prescribed rest period. Instead of a percentage value or in addition thereto, the indication may also include a progress bar or similar graphical indication illustrating the difference between the past duration of the ongoing rest period and the duration of the prescribed rest period.

In addition to the aforementioned information, the relevant information from the environmental prescription, i.e. the currently relevant period of time and the duration of the rest period prescribed for that period of time, and an information indicative of the noise level derived from the measurement signal may be output by the output unit 9 as in the case the evaluation module 7 has determined that no rest period is in progress.

By means of the aforementioned information output by the output unit 9, the healthcare staff can particularly be informed about an ongoing rest period of the patient 1 and about the time for the rest period to be maintained in order to fulfill the environmental prescription. On the basis of this information, the healthcare staff can plan its activities, such as visits to the patient 1, in such a way that the patient 1 receives the prescribed rest period substantially with the prescribed duration.

In particular, the healthcare staff may completely refrain from activities potentially disturbing the patient during a detected ongoing rest period and may schedule such activities for a point in time when the minimum duration has expired for the ongoing rest period. Or, in accordance with the a less strict strategy, the healthcare staff may plan activities in such a way that an ongoing rest period with a past duration of a significant length but also with a significant difference to the duration of the prescribed rest period is not interrupted. Hereby, it is possible for the patient 1 to extend the ongoing rest period substantially to the prescribed duration and it is not necessary to begin a new rest period in order to fulfill the environmental prescription. On the other hand, the healthcare staff may still consider to interrupt an ongoing rest period with a past duration of a small length, such as a length of some minutes for example. In this situation, only a short duration of the rest period is "wasted" and the patient can still receive the prescribed rest period easily after the interruption. Moreover, the healthcare staff may consider to interrupt an ongoing rest period that has nearly reached the prescribed duration, because the exact fulfillment of the environmental prescription may not be required. Other strategies of the healthcare staff to plan its activities based on the information provided by the monitoring system are of course also possible.

In order to further assist the healthcare staff in planning its activities in accordance with the latter strategy, the evaluation module 7 may categorize the determined past duration of a detected ongoing rest period in each evaluation step in one embodiment of the monitoring system. In this embodiment, at least two categories may be provided: a first category which corresponds to a situation in which an interruption of the rest period is not preferable but may be considered, and a second category corresponding to a situation in which greater efforts should be made to avoid an interruption of an ongoing rest period. In accordance with the strategy described above, the first category may be allocated if the determined past duration of the ongoing rest period is below a predetermined first threshold. As explained above, this threshold may e.g. be set to several minutes. In particular, the first threshold may e.g. be between 2 and 15 minutes. In addition, the first category may be allocated if the ratio between the determined portion of past duration of the ongoing rest period and the duration of the prescribed rest period is above a predetermined second threshold. For example, the second threshold may be between 85% and 99%. When the aforementioned conditions are not fulfilled, i.e. when the determined past duration of the ongoing rest period is above the first threshold and when the radio between this duration and the duration of the prescribed rest period is below the second threshold, the second category may be allocated.

In case the evaluation module 7 is configured to allocate categories in such a way, it may control the output unit 9 to provide an indication representative of the allocated category in each evaluation step. On the basis of this indication, the healthcare staff can more easily determine whether an interruption of the ongoing rest period could be acceptable. In one embodiment, the indication comprises a color for presenting the output information or a part thereof at the output unit 9. For instance, the output unit 9 may display the information or a part thereof in a yellow color in case the first category is allocated and in a red color in case the second category is allocated.

In the way described above, the evaluation module 7 is capable of detecting and ongoing rest period and of comparing the past duration of a detected ongoing rest period with the relevant minimum duration specified in the environmental prescription. Moreover the evaluation module 7 is capable of detecting that the duration of an ongoing rest period has reached the minimum duration specified in the environmental prescription. In particular, the evaluation module 7 detects such a situation when the determined past duration of the ongoing rest period is equal to or larger than the prescribed minimum duration. In this case, the evaluation module 7 may control the output unit 9 to output a corresponding information. On the basis of this information, the healthcare staff may decide to perform a potentially disturbing activity, for example.

Upon having determined a duration of the ongoing rest period that is equal to or larger than the prescribed duration, the evaluation module 7 may proceed with the evaluation in the remaining portion of the relevant period of time specified in the environmental prescription. Further, it may control the output unit 9 to output an information that the environmental prescription for the patient is fulfilled with respect to the ongoing period of time.

Alternatively, the evaluation module 7 may proceed with the evaluation in the way described above without comparing the determined duration of the rest period with the duration for the rest period specified in the environmental prescription. This does particularly mean that the evaluation module 7 proceeds with the determination whether or not a rest period is in process on the basis of the prescribed noise threshold. And in case a rest period is detected, it may determine the past duration of the rest period. This past duration may be output by the output unit 9 in order to inform the healthcare staff about an ongoing rest period and its past duration. On the basis of this information, the healthcare staff can plan activities such that disturbances of the patient 1 are minimized also in case the environmental prescription for the patient is fulfilled.

In both aforementioned embodiments, the previously described evaluation of the measurement signal including the comparison of the determined past duration of an ongoing rest period with the prescribed duration is made again in the subsequent period of time specified in the environmental prescription.

Further, when the evaluation module 7 has detected on ongoing rest period in one evaluation step and when in the next evaluation step a noise level is derived from the measurement signal, which is above the relevant prescribed noise threshold, the ongoing rest period of the patient 1 has ended.

In this case the evaluation module 7 terminates the determination of the duration of the rest period. This determination is started again for the next detected rest period. Thus, in the embodiments described above, the evaluation module 7 may reset the timer (i.e. set the timer to zero) when it determines that the noise level derived from the measurement signal exceeds the relevant maximum noise level in one evaluation step after is has been below the maximum noise level in the preceding evaluation step. Or, the evaluation module 7 deletes the stored start time of the terminated rest period or marks the stored start time accordingly. Consequently, the evaluation module 7 can judge in each evaluation step that a rest period is in process if the timer is running (i.e. has a non-zero value) or the start time of the rest period is stored in the evaluation module 7 in an appropriate form (e.g. without a marking that the associated rest period has been terminated).

Moreover, the evaluation module 7 proceeds as explained above with the detection of rest periods of the patient 1 and with the control of the output unit 9 to output the aforementioned information upon having detected the termination of a rest period.

Figure 2:
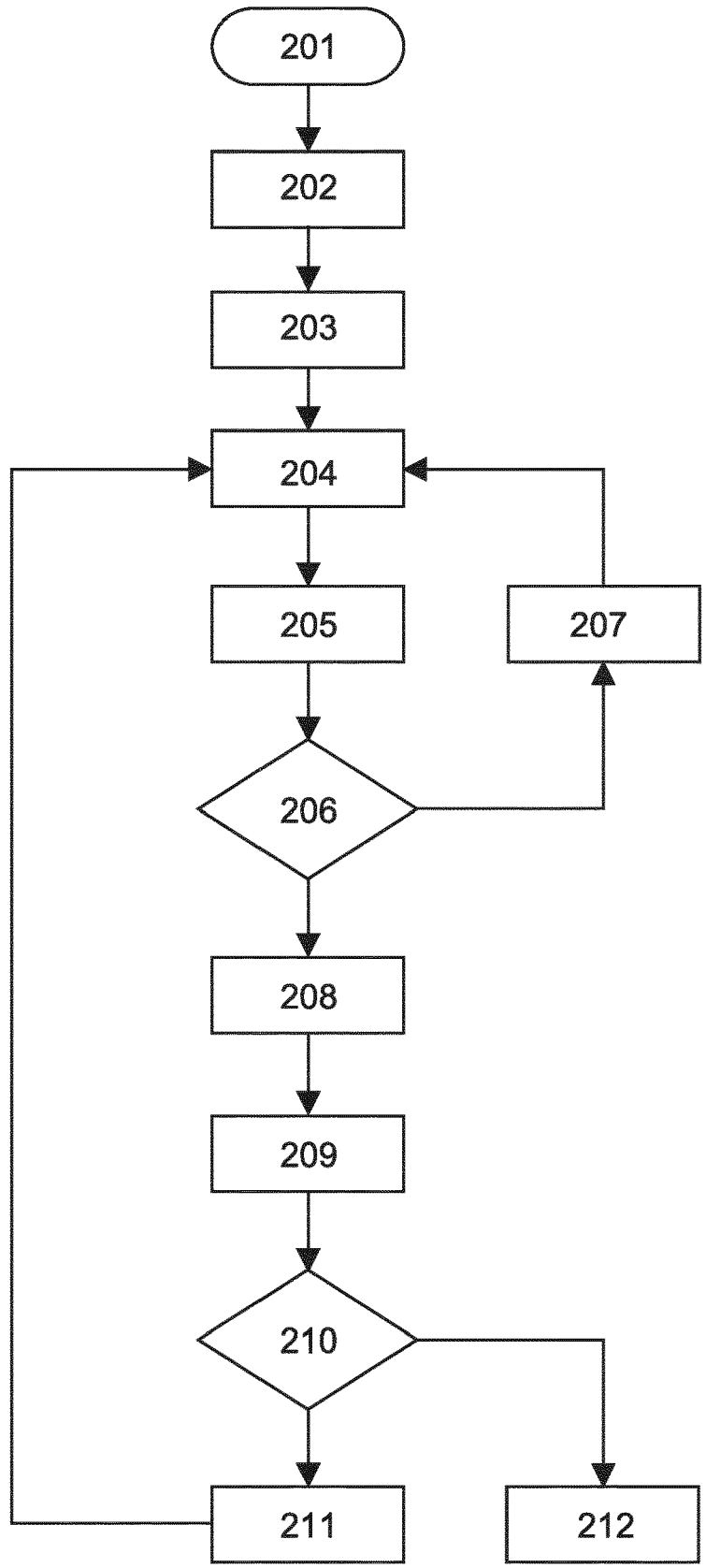
FIG. 2 shows schematically and exemplarily steps of an embodiment of a method for monitoring the exposure of a patient to an environmental factor carried out using the monitoring system shown in FIG. 1.

FIG. 2 illustrates steps of an embodiment of a method for monitoring the exposure of a patient to noise as it may be carried out in the monitoring system described above.

After the start of the method in step 201, the measurement signal representing the variation of noise in the vicinity of the patient 1 with time is captured by the measurement device 2 in step 202. Thereupon, the measurement signal is transmitted to the evaluation module 7. In order to evaluate the measurement signal, the evaluation module 7 obtains from the prescription database 8 the environmental prescription for the patient 1 in step 203. From the obtained environmental prescription, the evaluation module 7 determines the duration of the rest period prescribed for the current period of time, i.e. the period of time in which the evaluation is carried out. Upon having received the measurement signal from the measurement device 2 in step 204 the evaluation module 7 derives a noise level from the measurement signal in step 205 in a way described above. Then, the evaluation module 7 compares the derived noise level with the noise threshold specified in the environmental prescription for the rest period in the current period of time. On the basis of this comparison, the evaluation module 7 judges in step 206 whether the noise level derived from the measurement signal is below the maximum noise level specified in the environmental prescription.

In case, the evaluation module 7 judges in step 206 that the derived noise level is not below the maximum noise level specified in the environmental prescription, it may control the output unit 9 to output information about the rest period specified in the environmental prescription. In particular, the evaluation module 7 may control the output unit 9 to provide an information that for the patient 1 a rest period of the given duration is specified within the given period of time (step 207). Then, the evaluation module 7 proceeds to step 204 in order to receive and evaluate the next portion of the measurement signal in the next evaluation step.

If the evaluation module 7 judges in step 206 that the noise level derived from the measurement signal is below the noise threshold specified in the environmental prescription, a rest period is in progress for the patient 1. In this case, the evaluation module 7 determines the past duration of the rest period in step 208. This determination includes the detection of a newly started rest period in case the noise level derived from the measurement signal has been above the noise threshold specified in the environmental prescription in the preceding evaluation step. Or, if the derived noise level has been below the noise threshold in the preceding evaluation step, the evaluation module 7 determines a time value corresponding to the past duration of the ongoing rest period in a way described above.

Thereupon, the evaluation module 7 compares the determined past duration of the detected ongoing rest period with the duration of the rest period specified in the environmental prescription (step 209) and judges in step 210 whether the past duration of the detected ongoing rest period is smaller than the duration of the rest period specified in the environmental prescription. If this is the case, the evaluation module 7 causes in step 211 the output unit 9 to output information representative of the result of the comparison made in step 209. As explained above, this information may include a time value corresponding to the difference between the determined past duration of the ongoing rest period and the duration of the prescribed rest period, or it may include a percentage value representing the portion of the prescribed rest period, which is elapsed within the ongoing rest period. In addition, the evaluation module 7 may categorize the difference between the determined duration of the ongoing rest period and the duration of the prescribed rest period in accordance with one of a plurality of predetermined categories. In this case, the evaluation module 7 may also control the output unit 9 to indicate the allocated category.

Then, the evaluation module 7 proceeds to step 204 in order to receive and evaluate the next portion of the measurement signal provided by the measurement device 2 in the next evaluation step.

In case the evaluation module 7 determines in step 210 that the past duration of the detected ongoing rest period is at least equal to the duration of the rest period specified in the environmental prescription, it determines that the environmental prescription is fulfilled for the current period of time in step 212 and proceeds in a way described above.

While the aforementioned embodiments particularly relate to the monitoring of the exposure of the patient 1 to noise, the invention is not so limited. Rather, the invention can also be used to monitor the exposure of the patient 1 to other environmental factors. In particular, the invention can be used to monitor the exposure of the patient to light. In this respect, the environmental prescription may specify periods in which the patient 1 should be exposed to a light intensity below a predetermined threshold. As in the embodiments described before with respect to periods in which the patient should not be exposed to noise above a threshold, the duration of the periods with a low light intensity and time frames in which such periods should occur can be specified in the environmental prescription. Moreover, it is likewise possible to specify an individual threshold value of the light intensity for the patient 1 and/or for each prescribed period with a low light intensity.

In order to determine the light intensity affecting the patient 1, the measurement device 2 may comprise a light sensor which may be positioned in the vicinity of the patient 1. The measurement signal provided by the measurement device 2 on the basis of the measurements of the light sensor may be provided to the evaluation module 7 and be evaluated by the evaluation module 7 in a similar way as in the embodiments described above.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system configured to monitor exposure of a patient to at least one environmental factor, comprising:
    a measurement device, comprising at least one of a noise sensor or a light sensor, configured to:
        monitor an environmental factor in a vicinity of the patient continuously or in small time intervals, and
        provide a measurement signal representing a level of the environmental factor in the vicinity of the patient;
    a processing unit comprising:
        a receiver module configured to receive the measurement signal from the measurement device;
        a prescription database configured to store an environmental prescription for the patient, the environmental prescription specifying a maximum level of the environmental factor and a prescribed minimum duration for the level of the environmental factor to be smaller than the maximum level for different rest periods, wherein the maximum level and the prescribed minimum duration for the different rest periods are specified individually for the patient based on the patient's ability to perceive the environmental factor or when the different rest periods occur; and
        an evaluation module configured to:
            determine, from the environmental prescription in the prescription database, the prescribed minimum duration of the environmental factor, and select the prescribed minimum duration of the environmental factor during a period of time which corresponds to a time of evaluation,
            evaluate the measurement signal in a plurality of consecutive evaluation steps during the time of evaluation,
            compare the level of the environmental factor derived from the measurement signal with the maximum level of the environmental factor during each step of the plurality of consecutive evaluation steps, wherein a timer is incremented in each step that the derived level is below the maximum level,
            detect a time interval, as measured by the timer, in which the level of the environmental factor is below the maximum level of the environmental factor, the time interval including one or more sections in which the level of the environmental factor exceeds the maximum level of the environmental factor for a period shorter than a predetermined duration, and
            compare a duration of the detected time interval with the prescribed minimum duration; and
    a display device configured to receive control signals from the evaluation module to display one indication of a plurality of indications, where each indication of the plurality of indications comprises a different color, and wherein each indication is representative of a result of the comparison between the duration of the detected time interval and the prescribed minimum duration, wherein:
        when the result of the comparison satisfies at least one condition, then the display displays a first indication of the plurality of indications signaling to a user that an interruption may be considered for the patient, and
        when the result of the comparison fails to satisfy the at least one condition, then the display displays a second indication of the plurality of indications signaling to the user that interruptions should be avoided for the patient.

2. The system as defined in claim 1, wherein the environmental factor is either noise or light.

3. The system as defined in claim 1, wherein the predetermined duration is defined as a function of the level of the environmental factor.

4. The system as defined in claim 1, wherein the environmental prescription specifies at least one period of time in which the level of the environmental factor should be smaller than the maximum level for the prescribed minimum duration and the evaluation module is further configured to check whether the level of the environmental factor is smaller than the maximum level for the prescribed minimum duration within the at least one period of time.

5. The system as defined in claim 4, wherein the at least one period of time corresponds to either a predetermined day or to predetermined hours on a certain day.

6. The system as defined in claim 4, wherein the evaluation module is further configured to: detect, in each of the different rest periods, a time interval in which the level of the environmental factor is below the maximum level associated with the rest period, and compare a duration of the detected time interval with the prescribed minimum duration associated with the rest period.

7. The system as defined in claim 1, wherein the prescription database is configured to store a further environmental prescription for a further patient, the further environmental prescription comprising a different maximum level of the environmental factor and a different minimum duration for the level of the environmental factor to be smaller than the maximum level.

8. The system as defined in claim 1, wherein the environmental factor is noise and the environmental prescription specifies individual maximum noise levels for sound categories of sound events, wherein the evaluation module is further configured to: detect a sound event based upon the measurement signal, determine a sound category for the detected sound event based upon an evaluation of a frequency spectrum of the measurement signal, and detect a time interval in which a level of the environmental factor is below the maximum level based upon a comparison between a noise level determined for the sound event and the maximum noise level specified for the sound category of the sound event.

9. The system as defined in claim 1, wherein the measurement device is comprised in a patient monitor configured to monitor at least one vital sign of the patient.

10. The system as defined in claim 1, wherein the indication of the plurality of indications that is representative of the result of the comparison comprises a ratio between the duration of the detected time interval and the prescribed minimum duration at each step of the plurality of consecutive evaluation steps.

11. The system as defined in claim 1, wherein the one or more sections of the detected time interval includes at least two sections in which the level of the environmental factor exceeds the maximum level of the environmental factor, and the at least two sections are separated by a predetermined minimum time distance.

12. The system as defined in claim 11, wherein the at least two sections include a first section of a first predetermined duration in which the level of the environmental factor exceeds the maximum level of the environmental factor by a first maximum amount and a second section of a second predetermined duration in which the level of the environmental factor exceeds the maximum level of the environmental factor by a second maximum amount.

13. The system as defined in claim 12, wherein the evaluation module is configured to determine when the level of the environmental factor exceeds an ultimate threshold value during the detected time interval and detect an end of the detected time interval regardless of whether the level of the environmental factor exceeds the ultimate threshold value during the first or second section.

14. The system as defined in claim 1, wherein the maximum level and the prescribed minimum duration for the different rest periods are specified individually for the patient based on when the different rest periods occur relative to a time when the patient is rendered less sensitive to the environmental factor.

15. A method for monitoring exposure of a patient to an environmental factor, the method comprising:
monitoring, by a measurement device comprising at least one of a noise sensor or a light sensor, an environmental factor in a vicinity of the patient continuously or in small time intervals;
providing, by the measurement device, a measurement signal representing a level of the environmental factor in the vicinity of the patient;
receiving, by a receiver module of a processing unit, the measurement signal from the measurement device;
obtaining, by the processing unit, an environmental prescription for the patient, the environmental prescription specifying a maximum level of the environmental factor and a prescribed minimum duration for the level of the environmental factor to be smaller than the maximum level for different rest periods, wherein the maximum level and the prescribed minimum duration for the different rest periods are specified individually for the patient based on the patient's ability to perceive the environmental factor or when the different rest periods occur;
determining, by an evaluation module of the processing unit, from the environmental prescription in a prescription database, the prescribed minimum duration of the environmental factor;
selecting, by the evaluation module, the prescribed minimum duration of the environmental factor during a period of time which corresponds to a time of evaluation;
evaluating, by the evaluation module, the measurement signal in a plurality of consecutive evaluation steps during the time of evaluation;
comparing, by the evaluation module, the level of the environmental factor derived from the measurement signal with the maximum level of the environmental factor during each step of the plurality of consecutive evaluation steps, wherein a timer is incremented in each step that the derived level is below the maximum level;
detecting, by the evaluation module, a time interval within the period of time, as measured by the timer, after the level of the environmental factor exceeds the maximum level of the environmental factor for a period longer than a predetermined duration;
comparing, by the evaluation module, a remaining duration of the period of time after the detected time interval with the prescribed minimum duration; and
displaying, on a display device configured to receive control signals from the evaluation module, an indication representative of a result of the comparison, so that a user is informed about a remaining amount of time until a rest period for the patient should begin.

16. The method as defined in claim 15, wherein the maximum level and the prescribed minimum duration for the different rest periods are specified individually for the patient based on when the different rest periods occur relative to a time when the patient is rendered less sensitive to the environmental factor.

17. A non-transitory computer-readable medium comprising instructions executable in a processing unit of a system to cause the processing unit to carry out a method of monitoring exposure of a patient to an environmental factor, the non-transitory computer-readable medium comprising:
instructions for receiving, by a receiver module of the processing unit, a measurement signal representing a level of the environmental factor in a vicinity of the patient, wherein the measurement signal is provided by a measurement device comprising at least one of a noise sensor or a light sensor configured to monitor the environmental factor in the vicinity of the patient continuously or in small time intervals;
instructions for obtaining, by the processing unit, an environmental prescription for the patient, the environmental prescription specifying a maximum level of the environmental factor and a prescribed minimum duration for the level of the environmental factor to be smaller than the maximum level for different rest periods, wherein the maximum level and the prescribed minimum duration for the different rest periods are specified individually for the patient based on the patient's ability to perceive the environmental factor or when the different rest periods occur;
instructions for determining, by an evaluation module of the processing unit, from the environmental prescription in a prescription database, the prescribed minimum duration of the environmental factor;

instructions for selecting, by the evaluation module, the prescribed minimum duration of the environmental factor during a period of time which corresponds to a time of evaluation;

instructions for evaluating, by the evaluation module, the measurement signal in a plurality of consecutive evaluation steps during the time of evaluation;

instructions for comparing, by the evaluation module, the level of the environmental factor derived from the measurement signal with the maximum level of the environmental factor during each step of the plurality of consecutive evaluation steps, wherein a timer is incremented in each step that the derived level is below the maximum level;

instructions for detecting, by the evaluation module, a time interval, as measured by the timer, in which the level of the environmental factor is below the maximum level of the environmental factor, the time interval including one or more sections in which the level of the environmental factor exceeds the maximum level of the environmental factor for a period shorter than a predetermined duration;

instructions for comparing, by the evaluation module, the duration of the detected time interval with the prescribed minimum duration; and instructions for displaying, on a display device configured to receive control signals from the evaluation module, one indication of a plurality of indications, where each indication of the plurality of indications comprises a different color, and wherein each indication is representative of a result of the comparison, wherein:
when the result of the comparison satisfies at least one condition, then the display displays a first indication of the plurality of indications signaling to a user that an interruption may be considered for the patient, and
when the result of the comparison fails to satisfy the at least one condition, then the display displays a second indication of the plurality of indications signaling to the user that interruptions should be avoided.

18. The non-transitory computer-readable medium as defined in claim 17, wherein the maximum level and the prescribed minimum duration for the different rest periods are specified individually for the patient based on when the different rest periods occur relative to a time when the patient is rendered less sensitive to the environmental factor.

* * * * *